United States Patent [19]
Reed

[11] Patent Number: 5,719,263
[45] Date of Patent: Feb. 17, 1998

[54] 230KD ANTIGEN PRESENT IN *LEISHMANIA* SPECIES

[75] Inventor: Steven G. Reed, Bellevue, Wash.

[73] Assignee: Corixa Corporation, Seattle, Wash.

[21] Appl. No.: 282,845

[22] Filed: Jul. 28, 1994

Related U.S. Application Data

[62] Division of Ser. No. 6,676, Jan. 15, 1993, Pat. No. 5,411,865.

[51] Int. Cl.$^6$ .................. A61K 38/17; A61K 39/008; C07K 14/44
[52] U.S. Cl. ............. 530/324; 530/350; 530/395; 424/191.1; 424/265.1; 424/266.1
[58] Field of Search .................... 424/191.1, 265.1, 424/266.1; 530/324, 350, 395

[56] References Cited

PUBLICATIONS

Burns et al., *Proc. Natl. Acad. Sci. USA* 90:775; 1993.
Zhang et al., *J. Clin. Microbiol.* 30:2788; 1992.
Reed et al., *Am. J. Trop. Med and Hygiene* 43:632; 1990.
Reed et al., *J. Immunol.* 138:1596; 1987.
Russo et al., *J. Immunol.* 147:3575; 1991.
Jaffe and Zallis, *Mol. Biochem. Parasitol.* 27:53; 1988.
Sheppard and Dwyer, *Mol. Biochem. Parasitol.* 19:35; 1986.
Wallace et al., *Infec. Immun.* 60:2688; 1992.
Blaxter et al., *Mol. Biochem. Parasitol.* 30:259; 1988.
Miller et al., *Mol. Biochem. Parasitol.* 39:267; 1990.
Sigma Catalog, pp. 1546–1548 1990.

*Primary Examiner*—Anthony C. Caputa
*Attorney, Agent, or Firm*—Seed and Berry LLP

[57] ABSTRACT

There is disclosed an isolated 230 Kd antigen which is present in *Leishmania chagasi* and *Leishmania donovani*, and an isolated polypeptide comprising one or a plurality of K39 repeat antigens. Also disclosed are DNAs encoding the 230 Kd antigen and the K39 repeat antigen, and vaccine compositions comprising the antigens.

2 Claims, 6 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 3319 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: rK39

( i x ) FEATURE:
        ( A ) NAME/KEY: CDS
        ( B ) LOCATION: 455..3319

( x i ) SEQUENCE DESCRIPTION: SEQ ID NO:1:

```
GCTCCCACGG  CGCTACCCCC  TTTCCGCAT  GTGCGACAGT  TTCACGCGTA  CAAACGTCTT      60

TCTCTCTCCT  TCGCGCGTGT  CGCTATGGGC  GGCGGCGCGT  CGGTGTCTTT  GATTGCACAG    120

CTCACCGCCT  CGCCATATTT  TCGTCGTGGC  CACGCGACCC  CCGACCTTC  CCCTCCTCCG    180

CCCCCAAAGA  CAAGCCAGAC  ATACCGACCA  TGCCGTCTGC  CCGCGTCTCT  GCTTACCAAG    240

CGCGCCACGC  ACCCCTTCCT  CGGCCCTGAA  TCTTTCGCGC  GGCGCCATAC  ATTGCATGCA    300

CGTCACTACG  CCTGTACACC  TTACACCTCC  TCTTGCCCAC  CCCTTTCCCC  TTCTACACGC    360

CTAACTACAC  ACACATATAT  ATATATATAT  ATAAAGCGCT  CAACGCACAC  ATACTGTGGC    420

CAGTATTACT  GCACCAACGT  CTGCCTCTTC  CAGG ATG CAC CCT TCC ACT GTG         472
                                        Met His Pro Ser Thr Val
                                          1               5
```

| | | | | | | | | | | | | | | | | |
|---|---|---|---|---|---|---|---|---|---|---|---|---|---|---|---|---|
| CGG | CGT | GAG | GCG | GAG | CGG | GTG | AAG | GTG | TCG | GTG | CGC | GTG | CGC | CCC | CTA | 520 |
| Arg | Arg | Glu | Ala | Glu | Arg | Val | Lys | Val | Ser | Val | Arg | Val | Arg | Pro | Leu | |
| | | | | 10 | | | | 15 | | | | | | 20 | | |
| AAC | GAA | CGT | GAA | AAC | AAT | GCC | CCG | GAA | GGG | ACG | AAA | GTG | ACC | GTT | GCG | 568 |
| Asn | Glu | Arg | Glu | Asn | Asn | Ala | Pro | Glu | Gly | Thr | Lys | Val | Thr | Val | Ala | |
| | | 25 | | | | | 30 | | | | | 35 | | | | |
| GCG | AAA | CAG | GCG | GCC | GCC | GTG | GTG | ACG | GTC | AAG | GTC | CTG | GGA | GGC | AGC | 616 |
| Ala | Lys | Gln | Ala | Ala | Ala | Val | Val | Thr | Val | Lys | Val | Leu | Gly | Gly | Ser | |
| | 40 | | | | | 45 | | | | | 50 | | | | | |
| AAC | AAC | AGC | GGC | GCC | GCC | GAG | TCG | ATG | GGG | ACT | GCA | AGG | CGG | GTA | GCG | 664 |
| Asn | Asn | Ser | Gly | Ala | Ala | Glu | Ser | Met | Gly | Thr | Ala | Arg | Arg | Val | Ala | |
| 55 | | | | | 60 | | | | | 65 | | | | | 70 | |
| CAG | GAC | TTT | CAG | TTC | GAC | CAC | GTG | TTC | TGG | TCT | GTG | GAG | ACG | CCG | GAC | 712 |
| Gln | Asp | Phe | Gln | Phe | Asp | His | Val | Phe | Trp | Ser | Val | Glu | Thr | Pro | Asp | |
| | | | | 75 | | | | | 80 | | | | | 85 | | |
| GCG | TGC | GGC | GCG | ACC | CCC | GCG | ACG | CAG | GCA | GAC | GTG | TTC | CGG | ACG | ATC | 760 |
| Ala | Cys | Gly | Ala | Thr | Pro | Ala | Thr | Gln | Ala | Asp | Val | Phe | Arg | Thr | Ile | |
| | | | 90 | | | | | 95 | | | | | 100 | | | |
| GGG | TAC | CCG | CTG | GTG | CAG | CAC | GCG | TTC | GAC | GGG | TTC | AAC | TCG | TGC | TTG | 808 |
| Gly | Tyr | Pro | Leu | Val | Gln | His | Ala | Phe | Asp | Gly | Phe | Asn | Ser | Cys | Leu | |
| | | 105 | | | | | 110 | | | | | 115 | | | | |
| TTT | GCG | TAC | GGG | CAG | ACA | GGG | AGC | GGG | AAG | ACG | TAC | ACG | ATG | ATG | GGC | 856 |
| Phe | Ala | Tyr | Gly | Gln | Thr | Gly | Ser | Gly | Lys | Thr | Tyr | Thr | Met | Met | Gly | |
| | 120 | | | | | 125 | | | | | 130 | | | | | |
| GCG | GAC | GTG | AGC | GCG | CTT | AGT | GGT | GAG | GGC | AAC | GGC | GTG | ACG | CCG | CGG | 904 |
| Ala | Asp | Val | Ser | Ala | Leu | Ser | Gly | Glu | Gly | Asn | Gly | Val | Thr | Pro | Arg | |
| 135 | | | | | 140 | | | | | 145 | | | | | 150 | |
| ATC | TGC | CTG | GAG | ATC | TTT | GCG | CGG | AAG | GCG | AGC | GTG | GAG | GCG | CAG | GGG | 952 |
| Ile | Cys | Leu | Glu | Ile | Phe | Ala | Arg | Lys | Ala | Ser | Val | Glu | Ala | Gln | Gly | |
| | | | | 155 | | | | | 160 | | | | | 165 | | |
| CAC | TCG | CGG | TGG | ATC | GTG | GAG | CTG | GGG | TAC | GTG | GAG | GTG | TAC | AAC | GAG | 1000 |
| His | Ser | Arg | Trp | Ile | Val | Glu | Leu | Gly | Tyr | Val | Glu | Val | Tyr | Asn | Glu | |
| | | | 170 | | | | | 175 | | | | | 180 | | | |
| CGC | GTG | TCG | GAC | CTG | CTT | GGG | AAG | CGG | AAG | AAG | GGT | GTG | AAG | GGC | GGC | 1048 |
| Arg | Val | Ser | Asp | Leu | Leu | Gly | Lys | Arg | Lys | Lys | Gly | Val | Lys | Gly | Gly | |
| | | 185 | | | | | 190 | | | | | 195 | | | | |
| GGC | GAG | GAG | GTG | TAC | GTG | GAC | GTG | CGC | GAG | CAC | CCG | AGC | CGC | GGC | GTG | 1096 |
| Gly | Glu | Glu | Val | Tyr | Val | Asp | Val | Arg | Glu | His | Pro | Ser | Arg | Gly | Val | |
| | 200 | | | | | 205 | | | | | 210 | | | | | |
| TTC | CTG | GAG | GGG | CAG | CGG | CTG | GTG | GAG | GTT | GGG | AGC | CTG | GAC | GAT | GTT | 1144 |
| Phe | Leu | Glu | Gly | Gln | Arg | Leu | Val | Glu | Val | Gly | Ser | Leu | Asp | Asp | Val | |
| 215 | | | | | 220 | | | | | 225 | | | | | 230 | |
| GTG | CGG | CTG | ATC | GAG | ATC | GGC | AAC | GGC | GTG | CGG | CAC | ACC | GCT | TCG | ACG | 1192 |
| Val | Arg | Leu | Ile | Glu | Ile | Gly | Asn | Gly | Val | Arg | His | Thr | Ala | Ser | Thr | |
| | | | | 235 | | | | | 240 | | | | | 245 | | |
| AAG | ATG | AAC | GAC | CGG | AGC | AGC | CGG | AGC | CAC | GCG | ATC | ATC | ATG | CTG | CTG | 1240 |
| Lys | Met | Asn | Asp | Arg | Ser | Ser | Arg | Ser | His | Ala | Ile | Ile | Met | Leu | Leu | |
| | | | 250 | | | | | 255 | | | | | 260 | | | |
| CTG | CGC | GAG | GAG | CGG | ACG | ATG | ACG | ACG | AAG | AGC | GGG | GAG | ACG | ATC | CGT | 1288 |
| Leu | Arg | Glu | Glu | Arg | Thr | Met | Thr | Thr | Lys | Ser | Gly | Glu | Thr | Ile | Arg | |
| | | 265 | | | | | 270 | | | | | 275 | | | | |
| ACT | GCC | GGC | AAG | AGC | AGC | CGC | ATG | AAC | CTT | GTG | GAC | CTT | GCG | GGG | TCT | 1336 |
| Thr | Ala | Gly | Lys | Ser | Ser | Arg | Met | Asn | Leu | Val | Asp | Leu | Ala | Gly | Ser | |
| | 280 | | | | | 285 | | | | | 290 | | | | | |
| GAG | CGC | GTG | GCG | CAG | TCG | CAG | GTG | GAG | GGG | CAG | CAG | TTC | AAG | GAG | GCG | 1384 |
| Glu | Arg | Val | Ala | Gln | Ser | Gln | Val | Glu | Gly | Gln | Gln | Phe | Lys | Glu | Ala | |
| 295 | | | | | 300 | | | | | 305 | | | | | 310 | |
| ACG | CAC | ATC | AAC | CTG | TCG | CTG | ACG | ACG | CTC | GGG | CGC | GTG | ATC | GAC | GTG | 1432 |
| Thr | His | Ile | Asn | Leu | Ser | Leu | Thr | Thr | Leu | Gly | Arg | Val | Ile | Asp | Val | |
| | | | | 315 | | | | | 320 | | | | | 325 | | |

| | | | | | | | | | | | | | | | | |
|---|---|---|---|---|---|---|---|---|---|---|---|---|---|---|---|---|
| CTC | GCG | GAC | ATG | GCG | ACG | AAG | GGT | GCG | AAG | GCG | CAG | TAC | AGC | GTT | GCG | 1480 |
| Leu | Ala | Asp | Met | Ala | Thr | Lys | Gly | Ala | Lys | Ala | Gln | Tyr | Ser | Val | Ala | |
| | | | 330 | | | | | 335 | | | | | 340 | | | |
| CCG | TTC | CGC | GAC | TCG | AAG | CTG | ACG | TTC | ATC | CTG | AAG | GAC | TCG | CTT | GGC | 1528 |
| Pro | Phe | Arg | Asp | Ser | Lys | Leu | Thr | Phe | Ile | Leu | Lys | Asp | Ser | Leu | Gly | |
| | | 345 | | | | | 350 | | | | | 355 | | | | |
| GGG | AAC | TCG | AAG | ACG | TTC | ATG | ATC | GCG | ACT | GTG | AGC | CCG | AGC | GCG | CTG | 1576 |
| Gly | Asn | Ser | Lys | Thr | Phe | Met | Ile | Ala | Thr | Val | Ser | Pro | Ser | Ala | Leu | |
| | 360 | | | | | 365 | | | | | 370 | | | | | |
| AAC | TAC | GAG | GAG | ACG | CTG | AGC | ACG | CTG | CGG | TAC | GCG | TCG | CGC | GCG | CGC | 1624 |
| Asn | Tyr | Glu | Glu | Thr | Leu | Ser | Thr | Leu | Arg | Tyr | Ala | Ser | Arg | Ala | Arg | |
| 375 | | | | | 380 | | | | | 385 | | | | | 390 | |
| GAC | ATT | GTG | AAT | GTT | GCG | CAG | GTG | AAC | GAG | GAC | CCG | CGC | GCA | CGG | CGG | 1672 |
| Asp | Ile | Val | Asn | Val | Ala | Gln | Val | Asn | Glu | Asp | Pro | Arg | Ala | Arg | Arg | |
| | | | | 395 | | | | | 400 | | | | | 405 | | |
| ATC | CGC | GAG | CTG | GAG | GAG | CAG | ATG | GAG | GAC | ATG | CGG | CAG | GCG | ATG | GCT | 1720 |
| Ile | Arg | Glu | Leu | Glu | Glu | Gln | Met | Glu | Asp | Met | Arg | Gln | Ala | Met | Ala | |
| | | | 410 | | | | | 415 | | | | | 420 | | | |
| GGC | GGC | GAC | CCC | GCG | TAC | GTG | TCT | GAG | CTG | AAG | AAG | AAG | CTT | GCG | CTG | 1768 |
| Gly | Gly | Asp | Pro | Ala | Tyr | Val | Ser | Glu | Leu | Lys | Lys | Lys | Leu | Ala | Leu | |
| | | 425 | | | | | 430 | | | | | 435 | | | | |
| CTG | GAG | TCG | GAG | GCG | CAG | AAG | CGT | GCG | GCG | GAC | CTG | CAG | GCG | CTG | GAG | 1816 |
| Leu | Glu | Ser | Glu | Ala | Gln | Lys | Arg | Ala | Ala | Asp | Leu | Gln | Ala | Leu | Glu | |
| | 440 | | | | | 445 | | | | | 450 | | | | | |
| AGG | GAG | CGG | GAG | CAC | AAC | CAG | GTG | CAG | GAG | CGG | CTG | CTG | CGC | GCG | ACG | 1864 |
| Arg | Glu | Arg | Glu | His | Asn | Gln | Val | Gln | Glu | Arg | Leu | Leu | Arg | Ala | Thr | |
| 455 | | | | | 460 | | | | | 465 | | | | | 470 | |
| GAG | GCG | GAG | AAG | AGC | GAG | CTG | GAG | TCG | CGT | GCG | GCT | GCG | CTG | CAG | GAG | 1912 |
| Glu | Ala | Glu | Lys | Ser | Glu | Leu | Glu | Ser | Arg | Ala | Ala | Ala | Leu | Gln | Glu | |
| | | | | 475 | | | | | 480 | | | | | 485 | | |
| GAG | ATG | ACC | GCG | ACT | CGA | CGG | CAG | GCG | GAC | AAG | ATG | CAG | GCG | CTG | AAC | 1960 |
| Glu | Met | Thr | Ala | Thr | Arg | Arg | Gln | Ala | Asp | Lys | Met | Gln | Ala | Leu | Asn | |
| | | | 490 | | | | | 495 | | | | | 500 | | | |
| CTG | CGG | CTG | AAG | GAA | GAG | CAG | GCG | CGC | AAG | GAG | CGC | GAG | CTG | CTG | AAA | 2008 |
| Leu | Arg | Leu | Lys | Glu | Glu | Gln | Ala | Arg | Lys | Glu | Arg | Glu | Leu | Leu | Lys | |
| | | 505 | | | | | 510 | | | | | 515 | | | | |
| GAG | ATG | GCG | AAG | AAG | GAC | GCC | GCG | CTC | TCG | AAG | GTT | CGG | CGA | CGC | AAA | 2056 |
| Glu | Met | Ala | Lys | Lys | Asp | Ala | Ala | Leu | Ser | Lys | Val | Arg | Arg | Arg | Lys | |
| | 520 | | | | | 525 | | | | | 530 | | | | | |
| GAC | GCC | GAG | ATA | GCA | AGC | GAG | CGC | GAG | AAG | CTG | GAG | TCG | ACC | GTG | GCG | 2104 |
| Asp | Ala | Glu | Ile | Ala | Ser | Glu | Arg | Glu | Lys | Leu | Glu | Ser | Thr | Val | Ala | |
| 535 | | | | | 540 | | | | | 545 | | | | | 550 | |
| CAG | CTG | GAG | CGT | GAG | CAG | CGC | GAG | CGC | GAG | GTG | GCT | CTG | GAC | GCA | TTG | 2152 |
| Gln | Leu | Glu | Arg | Glu | Gln | Arg | Glu | Arg | Glu | Val | Ala | Leu | Asp | Ala | Leu | |
| | | | | 555 | | | | | 560 | | | | | 565 | | |
| CAG | ACG | CAC | CAG | AGA | AAG | CTG | CAG | GAA | GCG | CTC | GAG | AGC | TCT | GAG | CGG | 2200 |
| Gln | Thr | His | Gln | Arg | Lys | Leu | Gln | Glu | Ala | Leu | Glu | Ser | Ser | Glu | Arg | |
| | | | 570 | | | | | 575 | | | | | 580 | | | |
| ACA | GCC | GCG | GAA | AGG | GAC | CAG | CTG | CTG | CAG | CAG | CTA | ACA | GAG | CTT | CAG | 2248 |
| Thr | Ala | Ala | Glu | Arg | Asp | Gln | Leu | Leu | Gln | Gln | Leu | Thr | Glu | Leu | Gln | |
| | | 585 | | | | | 590 | | | | | 595 | | | | |
| TCT | GAG | CGT | ACG | CAG | CTA | TCA | CAG | GTT | GTG | ACC | GAC | CGC | GAG | CGG | CTT | 2296 |
| Ser | Glu | Arg | Thr | Gln | Leu | Ser | Gln | Val | Val | Thr | Asp | Arg | Glu | Arg | Leu | |
| | 600 | | | | | 605 | | | | | 610 | | | | | |
| ACA | CGC | GAC | TTG | CAG | CGT | ATT | CAG | TAC | GAG | TAC | GGG | GAA | ACC | GAG | CTC | 2344 |
| Thr | Arg | Asp | Leu | Gln | Arg | Ile | Gln | Tyr | Glu | Tyr | Gly | Glu | Thr | Glu | Leu | |
| 615 | | | | | 620 | | | | | 625 | | | | | 630 | |
| GCG | CGA | GAC | GTG | GCG | CTG | TGC | GCC | GCG | CAG | GAG | ATG | GAG | GCG | CGC | TAC | 2392 |
| Ala | Arg | Asp | Val | Ala | Leu | Cys | Ala | Ala | Gln | Glu | Met | Glu | Ala | Arg | Tyr | |
| | | | | 635 | | | | | 640 | | | | | 645 | | |

```
CAC GCT GCT GTG TTT CAC CTG CAA ACG CTC CTG GAG CTC GCA ACC GAG       2440
His Ala Ala Val Phe His Leu Gln Thr Leu Leu Glu Leu Ala Thr Glu
            650                 655                 660

TGG GAG GAC GCA CTC CGC GAG CGT GCG CTT GCA GAG CGT GAC GAA GCC       2488
Trp Glu Asp Ala Leu Arg Glu Arg Ala Leu Ala Glu Arg Asp Glu Ala
        665                 670                 675

GCT GCA GCC GAA CTT GAT GCC GCA GCC TCT ACT TCC CAA AAC GCA CGT       2536
Ala Ala Ala Glu Leu Asp Ala Ala Ala Ser Thr Ser Gln Asn Ala Arg
    680                 685                 690

GAA AGC GCC TGC GAG CGG CTA ACC AGC CTT GAG CAG CAG CTT CGC GAA       2584
Glu Ser Ala Cys Glu Arg Leu Thr Ser Leu Glu Gln Gln Leu Arg Glu
695                 700                 705                 710

TCC GAG GAG CGC GCT GCG GAG CTG GCG AGC CAG CTG GAG GCC ACT GCT       2632
Ser Glu Glu Arg Ala Ala Glu Leu Ala Ser Gln Leu Glu Ala Thr Ala
                715                 720                 725

GCT GCG AAG TCG TCG GCG GAG CAG GAC CGC GAG AAC ACG AGG GCC ACG       2680
Ala Ala Lys Ser Ser Ala Glu Gln Asp Arg Glu Asn Thr Arg Ala Thr
            730                 735                 740

CTA GAG CAG CAG CTT CGC GAA TCC GAG GCG CGC GCT GCG GAG CTG GCG       2728
Leu Glu Gln Gln Leu Arg Glu Ser Glu Ala Arg Ala Ala Glu Leu Ala
        745                 750                 755

AGC CAG CTG GAG GCC ACT GCT GCT GCG AAG ATG TCA GCG GAG CAG GAC       2776
Ser Gln Leu Glu Ala Thr Ala Ala Ala Lys Met Ser Ala Glu Gln Asp
    760                 765                 770

CGC GAG AAC ACG AGG GCC ACG CTA GAG CAG CAG CTT CGT GAC TCC GAG       2824
Arg Glu Asn Thr Arg Ala Thr Leu Glu Gln Gln Leu Arg Asp Ser Glu
775                 780                 785                 790

GAG CGC GCT GCG GAG CTG GCG AGC CAG CTG GAG TCC ACT ACT GCT GCG       2872
Glu Arg Ala Ala Glu Leu Ala Ser Gln Leu Glu Ser Thr Thr Ala Ala
                795                 800                 805

AAG ATG TCA GCG GAG CAG GAC CGC GAG AGC ACG AGG GCC ACG CTA GAG       2920
Lys Met Ser Ala Glu Gln Asp Arg Glu Ser Thr Arg Ala Thr Leu Glu
            810                 815                 820

CAG CAG CTT CGT GAC TCC GAG GAG CGC GCT GCG GAG CTG GCG AGC CAG       2968
Gln Gln Leu Arg Asp Ser Glu Glu Arg Ala Ala Glu Leu Ala Ser Gln
        825                 830                 835

CTG GAG TCC ACT ACT GCT GCG AAG ATG TCA GCG GAG CAG GAC CGC GAG       3016
Leu Glu Ser Thr Thr Ala Ala Lys Met Ser Ala Glu Gln Asp Arg Glu
    840                 845                 850

AGC ACG AGG GCC ACG CTA GAG CAG CAG CTT CGC GAA TCC GAG GAG CGC       3064
Ser Thr Arg Ala Thr Leu Glu Gln Gln Leu Arg Glu Ser Glu Glu Arg
855                 860                 865                 870

GCT GCG GAG CTG GCG AGC CAG CTG GAG TCC ACT ACT GCT GCG AAG ATG       3112
Ala Ala Glu Leu Ala Ser Gln Leu Glu Ser Thr Thr Ala Ala Lys Met
                875                 880                 885

TCA GCG GAG CAG GAC CGC GAG AGC ACG AGG GCC ACG CTA GAG CAG CAG       3160
Ser Ala Glu Gln Asp Arg Glu Ser Thr Arg Ala Thr Leu Glu Gln Gln
            890                 895                 900

CTT CGT GAC TCC GAG GAG CGC GCT GCG GAG CTG GCG AGC CAG CTG GAG       3208
Leu Arg Asp Ser Glu Glu Arg Ala Ala Glu Leu Ala Ser Gln Leu Glu
        905                 910                 915

GCC ACT GCT GCT GCG AAG TCG TCG GCG GAG CAG GAC CGC GAG AAC ACG       3256
Ala Thr Ala Ala Ala Lys Ser Ser Ala Glu Gln Asp Arg Glu Asn Thr
    920                 925                 930

AGG GCC GCG TTG GAG CAG CAG CTT CGT GAC TCC GAG GAG CGC GCC GCG       3304
Arg Ala Ala Leu Glu Gln Gln Leu Arg Asp Ser Glu Glu Arg Ala Ala
935                 940                 945                 950

GAG CTG GCG AGC CAG                                                   3319
Glu Leu Ala Ser Gln
            955
```

( 2 ) INFORMATION FOR SEQ ID NO:2:

( i ) SEQUENCE CHARACTERISTICS:
        ( A ) LENGTH: 955 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met His Pro Ser Thr Val Arg Arg Glu Ala Glu Arg Val Lys Val Ser
 1               5                  10                  15

Val Arg Val Arg Pro Leu Asn Glu Arg Glu Asn Asn Ala Pro Glu Gly
                20                  25                  30

Thr Lys Val Thr Val Ala Ala Lys Gln Ala Ala Ala Val Val Thr Val
             35                  40                  45

Lys Val Leu Gly Gly Ser Asn Asn Ser Gly Ala Ala Glu Ser Met Gly
     50                  55                  60

Thr Ala Arg Arg Val Ala Gln Asp Phe Gln Phe Asp His Val Phe Trp
 65                  70                  75                  80

Ser Val Glu Thr Pro Asp Ala Cys Gly Ala Thr Pro Ala Thr Gln Ala
                 85                  90                  95

Asp Val Phe Arg Thr Ile Gly Tyr Pro Leu Val Gln His Ala Phe Asp
                100                 105                 110

Gly Phe Asn Ser Cys Leu Phe Ala Tyr Gly Gln Thr Gly Ser Gly Lys
                115                 120                 125

Thr Tyr Thr Met Met Gly Ala Asp Val Ser Ala Leu Ser Gly Glu Gly
    130                 135                 140

Asn Gly Val Thr Pro Arg Ile Cys Leu Glu Ile Phe Ala Arg Lys Ala
145                 150                 155                 160

Ser Val Glu Ala Gln Gly His Ser Arg Trp Ile Val Glu Leu Gly Tyr
                165                 170                 175

Val Glu Val Tyr Asn Glu Arg Val Ser Asp Leu Leu Gly Lys Arg Lys
                180                 185                 190

Lys Gly Val Lys Gly Gly Gly Glu Glu Val Tyr Val Asp Val Arg Glu
            195                 200                 205

His Pro Ser Arg Gly Val Phe Leu Glu Gly Gln Arg Leu Val Glu Val
    210                 215                 220

Gly Ser Leu Asp Asp Val Val Arg Leu Ile Glu Ile Gly Asn Gly Val
225                 230                 235                 240

Arg His Thr Ala Ser Thr Lys Met Asn Asp Arg Ser Ser Arg Ser His
                245                 250                 255

Ala Ile Ile Met Leu Leu Leu Arg Glu Glu Arg Thr Met Thr Thr Lys
                260                 265                 270

Ser Gly Glu Thr Ile Arg Thr Ala Gly Lys Ser Ser Arg Met Asn Leu
            275                 280                 285

Val Asp Leu Ala Gly Ser Glu Arg Val Ala Gln Ser Gln Val Glu Gly
    290                 295                 300

Gln Gln Phe Lys Glu Ala Thr His Ile Asn Leu Ser Leu Thr Thr Leu
305                 310                 315                 320

Gly Arg Val Ile Asp Val Leu Ala Asp Met Ala Thr Lys Gly Ala Lys
                325                 330                 335

Ala Gln Tyr Ser Val Ala Pro Phe Arg Asp Ser Lys Leu Thr Phe Ile
                340                 345                 350

Leu Lys Asp Ser Leu Gly Gly Asn Ser Lys Thr Phe Met Ile Ala Thr
```

-continued

|     |     | 355 |     |     |     |     | 360 |     |     |     |     | 365 |     |     |
|-----|-----|-----|-----|-----|-----|-----|-----|-----|-----|-----|-----|-----|-----|-----|
| Val | Ser | Pro | Ser | Ala | Leu | Asn | Tyr | Glu | Glu | Thr | Leu | Ser | Thr | Leu | Arg |
|     | 370 |     |     |     |     | 375 |     |     |     |     | 380 |     |     |     |
| Tyr | Ala | Ser | Arg | Ala | Arg | Asp | Ile | Val | Asn | Val | Ala | Gln | Val | Asn | Glu |
| 385 |     |     |     | 390 |     |     |     |     | 395 |     |     |     |     | 400 |
| Asp | Pro | Arg | Ala | Arg | Arg | Ile | Arg | Glu | Leu | Glu | Glu | Gln | Met | Glu | Asp |
|     |     |     |     | 405 |     |     |     |     | 410 |     |     |     | 415 |     |
| Met | Arg | Gln | Ala | Met | Ala | Gly | Gly | Asp | Pro | Ala | Tyr | Val | Ser | Glu | Leu |
|     |     |     | 420 |     |     |     |     | 425 |     |     |     |     | 430 |     |
| Lys | Lys | Lys | Leu | Ala | Leu | Leu | Glu | Ser | Glu | Ala | Gln | Lys | Arg | Ala | Ala |
|     |     | 435 |     |     |     |     | 440 |     |     |     |     | 445 |     |     |
| Asp | Leu | Gln | Ala | Leu | Glu | Arg | Glu | Arg | Glu | His | Asn | Gln | Val | Gln | Glu |
|     | 450 |     |     |     |     | 455 |     |     |     |     | 460 |     |     |     |
| Arg | Leu | Leu | Arg | Ala | Thr | Glu | Ala | Glu | Lys | Ser | Glu | Leu | Glu | Ser | Arg |
| 465 |     |     |     |     | 470 |     |     |     |     | 475 |     |     |     |     | 480 |
| Ala | Ala | Ala | Leu | Gln | Glu | Glu | Met | Thr | Ala | Thr | Arg | Arg | Gln | Ala | Asp |
|     |     |     |     | 485 |     |     |     |     | 490 |     |     |     |     | 495 |
| Lys | Met | Gln | Ala | Leu | Asn | Leu | Arg | Leu | Lys | Glu | Glu | Gln | Ala | Arg | Lys |
|     |     |     | 500 |     |     |     |     | 505 |     |     |     |     | 510 |     |
| Glu | Arg | Glu | Leu | Leu | Lys | Glu | Met | Ala | Lys | Lys | Asp | Ala | Ala | Leu | Ser |
|     |     | 515 |     |     |     |     | 520 |     |     |     |     | 525 |     |     |
| Lys | Val | Arg | Arg | Arg | Lys | Asp | Ala | Glu | Ile | Ala | Ser | Glu | Arg | Glu | Lys |
|     | 530 |     |     |     |     | 535 |     |     |     |     | 540 |     |     |     |
| Leu | Glu | Ser | Thr | Val | Ala | Gln | Leu | Glu | Arg | Glu | Gln | Arg | Glu | Arg | Glu |
| 545 |     |     |     |     | 550 |     |     |     |     | 555 |     |     |     |     | 560 |
| Val | Ala | Leu | Asp | Ala | Leu | Gln | Thr | His | Gln | Arg | Lys | Leu | Gln | Glu | Ala |
|     |     |     |     | 565 |     |     |     |     | 570 |     |     |     |     | 575 |
| Leu | Glu | Ser | Ser | Glu | Arg | Thr | Ala | Ala | Glu | Arg | Asp | Gln | Leu | Leu | Gln |
|     |     |     | 580 |     |     |     |     | 585 |     |     |     |     | 590 |     |
| Gln | Leu | Thr | Glu | Leu | Gln | Ser | Glu | Arg | Thr | Gln | Leu | Ser | Gln | Val | Val |
|     |     | 595 |     |     |     |     | 600 |     |     |     |     | 605 |     |     |
| Thr | Asp | Arg | Glu | Arg | Leu | Thr | Arg | Asp | Leu | Gln | Arg | Ile | Gln | Tyr | Glu |
|     | 610 |     |     |     |     | 615 |     |     |     |     | 620 |     |     |     |
| Tyr | Gly | Glu | Thr | Glu | Leu | Ala | Arg | Asp | Val | Ala | Leu | Cys | Ala | Ala | Gln |
| 625 |     |     |     |     | 630 |     |     |     |     | 635 |     |     |     |     | 640 |
| Glu | Met | Glu | Ala | Arg | Tyr | His | Ala | Ala | Val | Phe | His | Leu | Gln | Thr | Leu |
|     |     |     |     | 645 |     |     |     |     | 650 |     |     |     |     | 655 |
| Leu | Glu | Leu | Ala | Thr | Glu | Trp | Glu | Asp | Ala | Leu | Arg | Glu | Arg | Ala | Leu |
|     |     |     | 660 |     |     |     |     | 665 |     |     |     |     | 670 |     |
| Ala | Glu | Arg | Asp | Glu | Ala | Ala | Ala | Ala | Glu | Leu | Asp | Ala | Ala | Ala | Ser |
|     |     | 675 |     |     |     |     | 680 |     |     |     |     | 685 |     |     |
| Thr | Ser | Gln | Asn | Ala | Arg | Glu | Ser | Ala | Cys | Glu | Arg | Leu | Thr | Ser | Leu |
|     | 690 |     |     |     |     | 695 |     |     |     |     | 700 |     |     |     |
| Glu | Gln | Gln | Leu | Arg | Glu | Ser | Glu | Glu | Arg | Ala | Ala | Glu | Leu | Ala | Ser |
| 705 |     |     |     |     | 710 |     |     |     |     | 715 |     |     |     |     | 720 |
| Gln | Leu | Glu | Ala | Thr | Ala | Ala | Ala | Lys | Ser | Ser | Ala | Glu | Gln | Asp | Arg |
|     |     |     |     | 725 |     |     |     |     | 730 |     |     |     |     | 735 |
| Glu | Asn | Thr | Arg | Ala | Thr | Leu | Glu | Gln | Gln | Leu | Arg | Glu | Ser | Glu | Ala |
|     |     |     | 740 |     |     |     |     | 745 |     |     |     |     | 750 |     |
| Arg | Ala | Ala | Glu | Leu | Ala | Ser | Gln | Leu | Glu | Ala | Thr | Ala | Ala | Ala | Lys |
|     |     | 755 |     |     |     |     | 760 |     |     |     |     | 765 |     |     |
| Met | Ser | Ala | Glu | Gln | Asp | Arg | Glu | Asn | Thr | Arg | Ala | Thr | Leu | Glu | Gln |
|     | 770 |     |     |     |     | 775 |     |     |     |     | 780 |     |     |     |

```
Gln  Leu  Arg  Asp  Ser  Glu  Glu  Arg  Ala  Ala  Glu  Leu  Ala  Ser  Gln  Leu
785                      790                     795                      800

Glu  Ser  Thr  Thr  Ala  Ala  Lys  Met  Ser  Ala  Glu  Gln  Asp  Arg  Glu  Ser
               805                      810                     815

Thr  Arg  Ala  Thr  Leu  Glu  Gln  Gln  Leu  Arg  Asp  Ser  Glu  Glu  Arg  Ala
               820                      825                     830

Ala  Glu  Leu  Ala  Ser  Gln  Leu  Glu  Ser  Thr  Thr  Ala  Ala  Lys  Met  Ser
          835                      840                     845

Ala  Glu  Gln  Asp  Arg  Glu  Ser  Thr  Arg  Ala  Thr  Leu  Glu  Gln  Gln  Leu
     850                      855                     860

Arg  Glu  Ser  Glu  Glu  Arg  Ala  Ala  Glu  Leu  Ala  Ser  Gln  Leu  Glu  Ser
865                      870                     875                      880

Thr  Thr  Ala  Ala  Lys  Met  Ser  Ala  Glu  Gln  Asp  Arg  Glu  Ser  Thr  Arg
               885                     890                      895

Ala  Thr  Leu  Glu  Gln  Gln  Leu  Arg  Asp  Ser  Glu  Glu  Arg  Ala  Ala  Glu
               900                     905                      910

Leu  Ala  Ser  Gln  Leu  Glu  Ala  Thr  Ala  Ala  Ala  Lys  Ser  Ser  Ala  Glu
          915                     920                      925

Gln  Asp  Arg  Glu  Asn  Thr  Arg  Ala  Ala  Leu  Glu  Gln  Gln  Leu  Arg  Asp
     930                     935                      940

Ser  Glu  Glu  Arg  Ala  Ala  Glu  Leu  Ala  Ser  Gln
945                     950                     955
```

( 2 ) INFORMATION FOR SEQ ID NO:3:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: protein ( i x ) FEATURE:
        ( D ) OTHER INFORMATION: Xaa at position 7 is Asp or Glu,
            at position 10 is Glu or Ala, at position 21 is Ala or
            Ser, at position 23 is Ala or Thr, at position 27 is Met
            or Ser, at position 35 is Asn or Ser, and at position 39
            is Thr or Ala.

( x i ) SEQUENCE DESCRIPTION: SEQ ID NO:3:

```
Leu  Glu  Gln  Gln  Leu  Arg  Xaa  Ser  Glu  Xaa  Arg  Ala  Ala  Glu  Leu  Ala
1                   5                     10                     15

Ser  Gln  Leu  Glu  Xaa  Thr  Xaa  Ala  Ala  Lys  Xaa  Ser  Ala  Glu  Gln  Asp
               20                    25                      30

Arg  Glu  Xaa  Thr  Arg  Ala  Xaa
          35
```

230KD ANTIGEN PRESENT IN *LEISHMANIA* SPECIES

CROSS REFERENCE TO RELATED APPLICATION

This application is a divisional application of U.S. patent application Ser. No. 08/006,676, filed Jan. 15, 1993, now issued as U.S. Pat. No. 5,411,865.

FIELD OF THE INVENTION

The present invention provides an isolated 230 Kd antigen which is present in *Leishmania chagasi* and *Leishmania donovani*, and DNAs encoding the antigen. The antigen is useful for detecting the presence of antibodies to Leishmania and as an immunogen.

BACKGROUND OF THE INVENTION

The transmission of pathogenic Leishmania involves an injection of extracellular promastigotes into a mammalian host by an infected sandfly. The promastigotes rapidly attach and enter monocytes and cells of the reticuloendothelial system, where they transform into amastigotes and multiply within phagolysosomes. Analysis of the interaction of Leishmania promastigotes with the target host cell suggests that both parasite and host molecules are involved in cell adhesion. Clinical symptoms of leishmaniasis range from self-healing skin lesions to diffuse cutaneous and mucosal manifestations, or severe visceral involvement of the spleen, liver and lymph nodes (visceral leishmaniasis or VL).

Visceral leishmaniasis is generally caused by *Leishmania donovani* in Africa and India, *L. infantum* in Southern Europe or *L. chagasi* in Latin America. In VL, high levels of parasite specific antibodies are observed prior to detection of antigen specific T cell responses (Ghose et al., *Clin. Exp. Immunol.* 40:318–326, 1980). This antibody response has been exploited for serodiagnosis of infection with *L. chagasi* and *L. donovani*. The current World Health Organization's estimate of 12 million cases of leishmaniasis and recent epidemics of visceral leishmaniasis in Sudan and India highlight the need for more effective early diagnosis and therapeutic agents. Also at least 400,000 new cases of VL are diagnosed annually. The current diagnostic tests to measure an antibody response use whole or lysed parasites. Therefore, there is a need in the art to improve the diagnostic accuracy for diagnosing VL early while the potentially fatal disease is more treatable.

Recovery from leishmaniasis correlates with the development of specific T lymphocyte responses and usually confers long-lasting immunity against reinfection (Carvalho et al., *J. Clin. Invest.* 76:2066–6, 1985 and Carvalho et al., *J. Immunol.* 135:4144–8, 1985). Both recovery from disease and resistance to reinfection are dependent on the development of specific T lymphocyte responses. Interferon gamma (IFN-γ) is a product of activated T cells, has demonstrated anti-leishmania activity in vitro (Murray et al., *J. Clin. Invest.* 72:1506, 1983 and Nacy et al., *J. Immunol.* 135:1305, 1985), and in vivo (Reed et al., *J. Immunol.* 132:3116, 1984 and Murray et al., *J. Immunol.* 1348:2290, 1987) and has been effectively in the clinical treatment of leishmaniasis (Harms et al., *Lancet* 10:1287, 1989 and Badaro et al., *N. Engl. J. Med.* 322:16, 1990).

One antigen, called gp63, has been cloned (Miller et al., *Mol. Biochem. Parasitol.* 38, 267–274, 1990) and was found to be a metalloprotease and is highly conserved among different species of Leishmania (Etges et al., *J. Biol. Chem.* 261:9098, 1986; Chaudhuri et at., *Mol. Biochem. Parasitol.* 27:43, 1988; Chaudhuri et al., *J. Biol. Chem.* 264:7483, 1989; Colmer-Gould et al., *J. Exp. Med.* 162:902, 1985; and Button et al., *J. Exp. Med.* 167:724, 1988). Gp63 is relatively abundant on both the infective promastigote stage and the intercellular amastigote stage (Frommel et al., *Mol. Biochem. Parasitol.* 38:25–32, 1990 and Medina-Acosta et al., *Mol. Biochem. Parasitol.* 37:263, 1989). Gp63 is important for both parasite entry into macrophages (Russel and Wilheim, *J. Immunol.* 136:2613, 1986; Chang et al., *Proc. Natl. Acad. Sci. USA* 83:100, 1986; Wilson and Hardin, *J. Immunol.* 141:265, 1988; and Mosser and Edelson *J. Immunol.* 135:2785, 1985) and subsequent survival within the phagosome (Chaudhuri et al., *J. Biol. Chem.* 264:7483, 1989). Immunization with native gp63 in vivo partially protected susceptible mice against cutaneous disease (Handman and Mitchell *Proc. Natl. Acad. Sci. USA* 82:5910, 1985 and Russel and Alexander *J. Immunol.* 140:1274, 1988). Moreover, recombinant gp63 expressed in Salmonella conferred partial protection by oral immunization against Leishmania major infection in resistant mice (Yang et al., *J. Immunol.* 145:2281, 1990). Both native gp63 and recombinant gp63 elicited strong proliferative responses, as well as IFN-γ production, from leishmaniasis patients with a spectrum of clinical disease (Russo et al., *J. Immunol.* 147:3575, 1991).

SUMMARY OF THE INVENTION

The present invention provides a method for diagnosing leishmaniasis comprising: (a) obtaining a sample from a patient suspected of being infected with a Leishmania parasite, wherein the sample contains antibodies from the patient; and (b) determining the presence of antibodies that bind to a K39 repeat unit antigen from the sample. Preferably the inventive method is a serodiagnostic method utilizing sera from the individual suspected of harboring a Leishmania parasite. Preferably the antigen used is one or a plurality of K39 repeat sequences, wherein the K39 repeat sequence comprises the amino acid sequence (in single letter designation) L E Q Q L R (D/E) S E (E/A) R A A E L A S Q L E (A/S) T (A/T) A A K (M/S) S A E Q D R E (N/S) T R A (T/A) or (in three letter designation) Leu Glu Gln Gln Leu Arg (Asp/Glu) Ser Glu (Glu/Ala) Arg Ala Ala Glu Leu Ala Ser Gln Leu Glu (Ala/Ser) Thr (Ala/Thr) Ala Ala Lys (Met/Ser) Ser Ala Glu Gln Asp Arg Glu (Asn/Ser) Thr Arg Ala (Thr/Ala) (SEQ ID NO:3).

The present invention further provides a diagnostic kit for evaluating a patient antibody-containing sample for the presence of anti-Leishmania parasite antibodies, comprising a K39 repeat unit antigen. Preferably, the K39 repeat unit antigen is bound to a solid phase. Preferably, the diagnostic kit further comprises an anti-human antibody conjugated to a detection moiety. Preferably the antigen used is one or a plurality of K39 repeat sequences, wherein the K39 repeat sequence comprises the amino acid sequence Leu Glu Gln Gln Leu Arg (Asp/Glu) Ser Glu (Glu/Ala) Arg Ala Ala Glu Leu Ala Ser Gln Leu Glu (Ala/Ser) Thr (Ala/Thr) Ala Ala Lys (Met/Ser) Ser Ala Glu Gln Asp Arg Glu (Asn/Ser) Thr Arg Ala (Thr/Ala) (SEQ ID NO:3).

BRIEF DESCRIPTION OF THE DRAWINGS AND SEQUENCES

FIG. 1 shows the expression and purification of recombinant K39 (rK39) antigen. The gels shows Coomassie blue-stained 12% SDS-polyacrylamide gel of molecular weight markers (lane 1), *E. coli* lysates from uninduced cells (lane 2), and induced cultures (lane 3) of clone K39, and purified rK39 (lane 4, 2 µg).

FIG. 2 shows reactivity of patient sera with rK39. Blots containing L. chagasi promastigote lysate (lane 1, 10 µg), purified rK39 (lane 2, 50 ng) and T. cruzi epimastigote lysate (lane 3, 10 µg) were probed with individual L. chagasi VL sera (A–C), individual L. donovani VL sera (D–F), or pooled mucosal leishmaniasis (G, n=4), cutaneous leishmaniasis (H, n=4), or T. cruzi infection (I, n=5) sera. Pooled normal human sera (n=3) and no primary antibody controls are shown (J and K, respectively). Bound antibody was detected with $^{125}$I-protein A.

FIGS. 3A and B shows a Southern blot analysis of the LcKin gene sequences. Genomic DNA (2.5 µg/lane) from L. chagasi digested with Bam HI (lane 1), Hind III (lane 2) and Psi I (lane 3) or Psi I digested DNA from L. amazonesis (lane 4), L. braziliensis (lane 5), L. guyanesis (lane 6), L. donovani (lane 7), L. infantum (lane 8), L. major (lane 9), or T. cruzi (lane 10) were analyzed by Southern blotting. The blots were probed (FIG. 3A) with a 2.4 kb Hind III fragment from the LcKin homology domain or (FIG. 3B) with the 915 bp repetitive insert of K39.

FIGS. 4A–C shows reactivity of rabbit anti-rK39 antiserum on recombinant and native leishmania lysates. FIG. 4A is an immunoblot of purified rK39 (50 ng per lane) transferred from 12% SDS-polyacrylamide gels and probed with preimmune rabbit serum (lane 1) or rabbit anti-rK39 (lane 2). FIG. 4B is an immunoblot of L. chagasi promastigote (lanes 1 and 5, 10 µg) and amastigote (lanes 2 and 6 10 µg) lysates or L. amazonensis promastigote (lanes 3 and 7, 10 µg) and amastigote (lanes 4 and 8, 10 µg) lysates, transferred from 7.5% SDS-polyacrylamide gels and probed with preimmune rabbit serum (lanes 1–4) or rabbit anti-rK39 (lanes 5–8). FIG. 4C is an immunoblot showing reactivity of rabbit antisera raised against L. chagasi ribosomal protein PO, described in Skeiky et al. (J. Exp. Med. 176:201, 1992), with lanes 1–4 of B.

FIG. 5A and B shows an ELISA evaluation of patient seroreactivity on L. chagasi promastigote lysate (FIG. 5A) or purified rK39 (FIG. 5B). Absorbance values (mean+ SEM) of Brazilian VL (VL-B, n=57), Sudanese VL (VL-S, n=52), T. cruzi infection (Tc, n=35), Brazilian cutaneous leishmaniasis (CL-B, n=13), Sudanese cutaneous leishmaniasis (CL-S, n=13) mucosal leishmaniasis (ML, n=15) and normal (n=15) sera.

FIG. 6 shows patient sera reactivities against recombinant gp63. All sera samples were diluted 1:100 and assayed by an ELISA technique. Individual absorbance values are represented by dots; horizontal and vertical bars represent the mean +/-95% confidence limit (Student's t-test), respectively. The abbreviations are visceral leishmaniasis (VL), cutaneous leishmaniasis (CL), and mucosal leishmaniasis (MCL).

SEQ ID NO: 1 is the nucleotide and amino acid sequence for a K39.

SEQ ID NO: 2 is the amino acid sequence of K39.

SEQ ID NO: 3 is the amino acid sequence of a 39 amino acid repeat unit antigen.

DETAILED DESCRIPTION OF THE INVENTION

The present invention provides a method for diagnosing VL and a diagnostic kit for VL. The present invention was made possible by the discovery of a K39 gene and its DNA sequence and deduced amino acid sequence having a plurality of antigenic 39 amino acid repeat units. The K39 gene was found in an attempt to characterize leishmania antigens recognized by a spectrum of VL patients, including VL patients infected with either L. donovani or L. chagasi.

Figure 1:
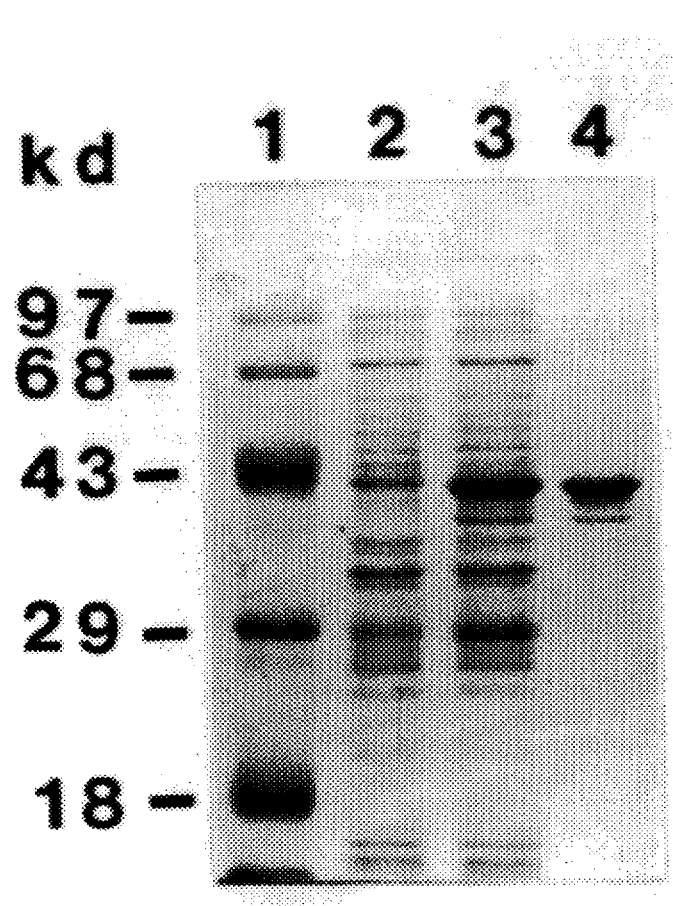

A L. chagasi genomic DNA expression library was screened with sera obtained from a patient having VL caused by L. donovani. From approximately 32,000 recombinants screened, seven clones were selected based upon reactivity with this patient's sera. The seven clones contained inserts ranging from 0.9 kb to 2.6 kb and expressed immunoreactive recombinant proteins of 35 kDa to 100 kDa. Clone K39 was exceptionally reactive with the test serum. Recombinant K39 antigen (rK39) migrated on Coomassie-stained SDS-PAGE as a 39 kDa protein in induced bacterial extracts (FIG. 1, lane 3). The protein was purified by ammonium sulfate fractionation and preparative isoelectric focusing (FIG. 1, lane 4) with a yield of 25–30 mg per liter.

The DNA and deduced amino acid sequences of the insert of clone K39 were determined and are provided in SEQ ID NOS: 1 and 2 herein. The DNA sequence contained a single open reading frame encoding 298 amino acids with a predicted molecular weight of 32.7 kDa and a pI of 4.4. Recombinant clone K39 contains an additional 6.2 kDa of plasmid fusion sequences. In this sequence was noted 6.5 copies of a randomly arrayed 39 amino acid repeat sequence. SEQ ID NO: 3 shows the consensus sequence of the repeat unit.

To further characterize this gene, clones containing sequences flanking the K39 gene fragment were isolated from the L. chagasi library using a K39 insert probe. Sequence analysis of one overlapping clone, LcKin, showed that the open reading frame extended for 1971 base pairs in the 5' direction, encoding 657 nonrepetitive amino acids. 5' to the putative ATG initiation codon, 454 base pairs of sequence were obtained with multiple termination codons in each reading frame. Partial characterization of clones containing 3' flanking sequences indicated that the repeat domain extended for approximately 3 to 4 kb.

GenPept and Swiss-Protein data bank searches revealed similarity between LcKin and several members of the superfamily of kinesin-related proteins, particularly in the N-terminal motor domain. A relatively high level of sequence conservation was observed in the putative ATP and microtubule binding domains (Yang et al., Cell 56:879, 1989). The remaining 500 residues showed little similarity to sequence of the tail regions of kinesin and myosin of a number of species. Secondary structure analysis predicted that this portion of LcKin (amino acids 426–955) contain greater than 90% helical structure, a feature characteristic of coiled-coil tail regions of several motor proteins. Therefore, the repetitive epitope of the rK39 antigen appears to be present in L. chagasi as part of the tail region of a leishmania kinesin-related protein.

The present invention provides an identification of a 230 kDa antigen of L. chagasi, LcKin, with sequence homology to the kinesin superfamily of motor proteins. The gene is predominantly expressed by tissue amastigotes. The DNA sequence is present in at least seven diverse species of Leishmania. The DNA sequence further comprises an extensive repetitive domain containing a 39 amino acid repeat unit. Southern analysis showed the repeat unit of LcKin to be variable among species, but was closely related in L. chagasi and L. donovani. Most significantly, there are high antibody liters in 98% of Brazilian VL patients to rK39, a recombinant antigen containing 6.46 copies of the 39 amino acid repeat sequence. Similar antibody levels were detected in 100% of tested Sudanese VL patients. These data indicate conservation of the repeat sequence between *L. chagasi* and *L. donovani*.

The present cloning of LcKin represents the first characterization of a gene encoding a protozoan motor protein. These microtuble based motors are involved in such varied intracellular processes as organelle and synaptic vesicle transport, chromosome segregation and spindle pole separation, nuclear fusion, protein sorting a flagellar beating. This tail domain is usually characterized by a predominantly alpha-helical structure which likely forms a coil interacting with different intracellular ligands which determine its function. The LcKin gene product is similar to members of this family in primary sequence, particularly in the putative ATP and microtubule binding domains, as well as in predicted secondary structure.

The inventive feature of LcKin was the high prevalence of antibody specific to the rK39 repeat sequence in VL patients from geographically distinct endemic regions of Brazil and the Sudan. Therefore, the rK39 repeat antigen is useful as a vaccine and as an antibody-binding antigen for a diagnostic kit for the detection and diagnosis of VL. Moreover, the inventive method for diagnosing VL using rK39 was specific for VL patients. False positives were not seen in normal patients, even normal patients from the endemic areas of Brazil and the Sudan. These data also reflect relatedness among members of the *L. donovani* complex. The data described herein provide a thorough analysis of patient antibody responses to a purified recombinant antigen (rK39) of *L. chagasi* and show a marked restriction of this response to *L. chagasi* and *L. donovani* infected patients with VL with 98% and 100% positivity in this group.. The inventive diagnostic kit and the inventive method for diagnosing VL and distinguishing VL from other infectious diseases with similar clinical presentations provides a needed tool in a clinicians hands in endemic areas of the world. Therefore, antibody reactivity to rK39 is an improved replacement for promastigote-based serological tests for the diagnosis of acute VL.

The rK39 antigen is an immunodominant B cell epitope comprising one or more copies of the Leu Glu Gln Gln Leu Arg (Asp/Glu) Ser Glu (Glu/Ala) Arg Ala Ala Glu Leu Ala Ser Gln Leu Glu (Ala/Ser) Thr (Ala/Thr) Ala Ala Lys (Met/Ser) Ser Ala Glu Gln Asp Arg Glu (Asn/Ser) Thr Arg Ala (Thr/Ala) 39 amino acid repeat sequence (SEQ ID NO:3). Preferably the K39 antigen comprises from 1 to about 7 copies of the 39 amino acid sequence. Most preferably, the K39 antigen comprises about 6 copies of this sequence.

Gp63 is a major surface glycoprotein of Leishmania parasites, is highly conserved among species and is expressed in both infective and intracellular stages. The gp63 gene of *L. chagasi* has been cloned, analyzed and described in Miller et al. (*Mol. Biochem. Parasitol.* 39:276, 1990). It is significant to note that the sequence of *L. chagasi* was found to differ significantly from that published for *L. major* (Button et al. *J. Exp. Med.* 167:724, 1988). The predicted protein sequences of gp63 from *L. major* and *L. chagasi* are closely related. Gp63 is a surface metalloprotease (Bouvier et al., *Mol Biochem. Parasitol.* 37:235, 1989 and Medina-Acosta et al., *Mol Biochem. Parasitol.* 37:263, 1989) that is also important for parasite entry into macrophages and survival within the phagosome. Native gp63 (ngp63) and recombinant gp63 (rgp63) elicited strong proliferative responses and IFN-γ production from leishmaniasis patients with a spectrum of clinical disease. The present invention further found the prevalence of gp63-specific antibodies among patients with clinically and geographically diverse leishmaniasis to provide a further useful diagnostic tool alone or in combination with the use of the K39 antigen for diagnosis of VL.

Figure 6:
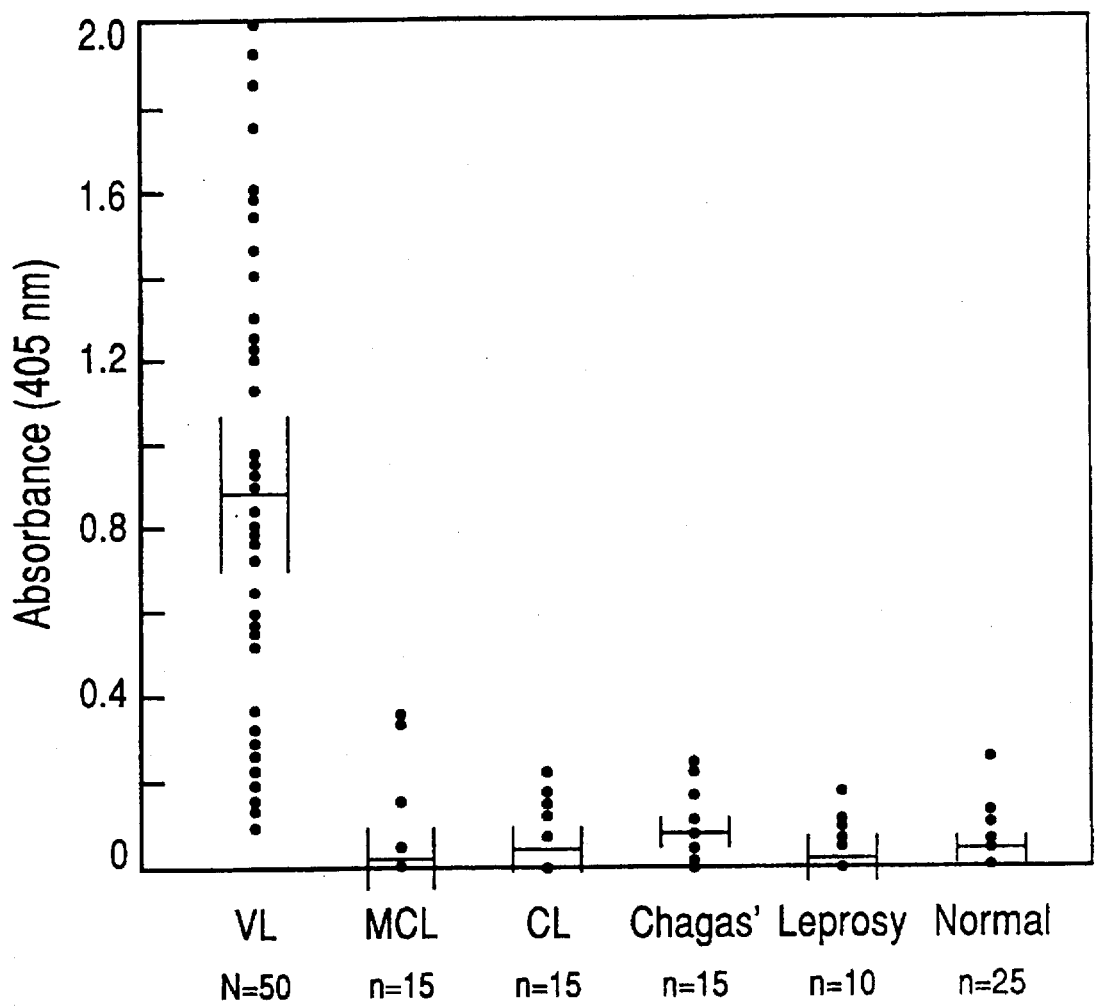

The prevalence of gp63-specific antibody among leishmaniasis and other disease groups was examined by an ELISA technique (described in Example 4 herein). All leishmaniasis sera were obtained from patients with active disease, and included Brazilian visceral, cutaneous or mucosal leishmaniasis from a study area in Bahia, Brazil or from biopsy-positive patients in the Sudan. Leprosy sera were from patients in Haiti where leishmaniasis has not been reported. Normal control sera were from normal volunteers in the US. FIG. 6 shows that there were elevated anti-gp63 antibody levels among VL patients (mean absorbance= 0.89). In fact, 84% ($^{42}/_{50}$) of the VL patient sera tested have absorbance values greater than 3 standard deviations above the mean of normal control sera. The remaining 16% had relatively low levels of gp63-specific antibody, despite generally high titers of leishmania-specific antibody (mean absorbance value of 1.54). In contrast, cutaneous and mucosal leishmaniasis patients showed very little seroreactivity with only two mucosal patients having absorbance values significantly above control normals. No sera samples from patients with a *T cruzi* infection or leprosy showed significantly elevated antibody levels to rgp63. These results indicate that gp63 is a potent B cell immunogen among VL patients although alone is not as good of an antigen in a diagnostic assay as is K39. However, the combination antigens of K39 and gp63 can provide a superior diagnostic kit with a reduced number of false positive results.

EXAMPLE 1

This example illustrates the cloning of the K39 antigen. A genomic library was constructed with mechanically sheared DNA of *L. chagasi* (MHOM/BR/82/BA-2,C1) in the expression vector lambda ZAPII according to the manufacturer's protocols (Stratagene, La Jolla, Calif.). Recombinants were screened with serum (obtained from a patient recently treated for acute *L. donovani* infection) preadsorbed to remove anti-*E. coli* reactivity according to the procedure described in Sambrook et al. *Molecular Cloning, A Laboratory Manual* 2nd Ed. (Cold Spring Harbor, N.Y., 1989).

The K39 clone was expressed to produce rK39 polypeptide and this was purified from a 25% to 40% ammonium sulfate fraction of a soluble bacterial lysate by preparative isoelectric focusing with a Bio-Rad Rotofor IEF cell and 1% 3/10 ampholytes (Bio-Rad, Richmond, Calif.) in the presence of 8M urea and 10 mM dithiothreitol. Peak fractions were concentrated by a second ammonium sulfate precipitation, and dialyzed against 25 mM Tris-HCl (pH 8), 150 mM NaCl (TBS). Protein concentrations were determined using a Pierce BCA protein assay (Pierce, Rockford, Ill.) and purity assessed by Coomassie-blue staining following SDS-PAGE.

A radiolabeled insert of K39 was used to screen the *L. chagasi* genomic library to obtain clones containing sequences flanking the K39 gene fragment. A set of overlapping deletions of clones K39 and LcKin were generated by controlled Exonuclease III digestion (according to the procedure described in Henikoff, *Gene* 28:351, 1984) to obtain a complete sequence of both the coding and noncoding strands. Single stranded template was prepared as described in Burns et al. (*Proc. Natl. Acad. Sci. USA* 89:1239, 1992) and nucleotide sequence was obtained by the Sanger dideoxynucleotide chain termination method using $^{35}$S-labeled dATP (Sanger et al., *Proc. Natl. Acad. Sci. USA*

74:5463, 1977) or by fluorescence-based sequencing on an Applied Biosystems Sequencer Model 373A, according to the manufacturer's protocols. Sequence comparisons were made with GenPept (72.0) and Swiss-Prot (22.0) with the Lipman/Pearson method (Pearson and Lipman, *Proc. Natl. Acad. Sci. USA* 85:2444, 1988). Secondary structural predictions were made according to Garner et al. (*J. Mol. Biol.* 120:97, 1978) and Chou et al. (*Advances in Enzymology* 47:45, 1978).

DNA from *Leishmania spp.* and *T. cruzi* (MHOM/CH/00/Tulahuen C2) were isolated, digested with Pst I, separated by agarose gel electrophoresis, and analyzed by Southern blotting. The blots were probed with a 2.4 kb Hind III fragment of LcKin derived from the 5' end of the gene (probe A) or a 915 bp insert of clone K39 (probe B). Each probe was radiolabeled with $\alpha$-$^{32}$P (dCTP) to a specific activity of $9 \times 10^8$ cpm/µg using random oligonucleotides as primers (Boehringer Mannheim, Indianapolis). The final washes were for 1 hr in 0.1× SSC/0.5% SDS at 68° C. Blots of *L. chagasi* DNA digested with Bam HI, Hind II and Pst I and no Hind III restriction sites were used and probed as above to assess gene copy. Probe A contained one Bam HI, one Pst I, and no Hind III restriction sites. Probe B did not contain sites for these restriction enzymes.

Figures 3A, 3B:
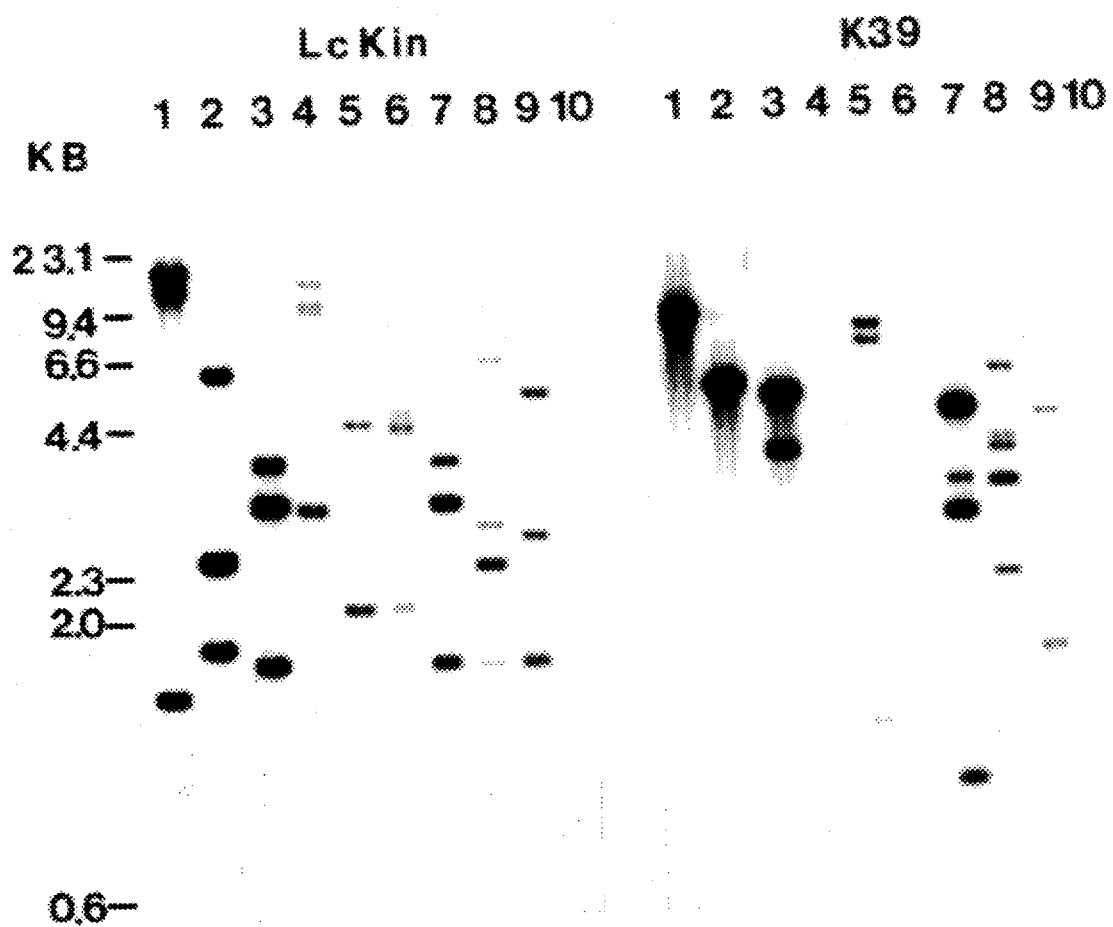

FIG. 3A shows the blot of probe A and FIG. 3B shows the blot of probe B. Probe A hybridized strongly to multiple Pst I restriction fragments of all *Leishmania spp.* tested (FIG. 3A, lanes 3-9), indicating conservation in the kinesin homology domain. Polymorphism in size and number of hybridizing restriction sites were noted. Less conservation in the repetitive domain of the LcKin gene was observed as probe B hybridized with varying intensity to Pst I restriction fragments of *L. chagasi* (MHOM/BR/82/BA-2,C1), *L. amazonensis* (IFLA/BR/67/PH8), *L. braziliensis* (MHOM/BR/75/M2903, obtained from Dr. Diane McMahon-Pratt, Yale University, New Haven, Conn.), *L. donovani* (MHOM/Et/67/HU3), *L. infantum* (IPT-1, obtained from Dr. Lee Schnur, Hebrew University-Hadassah Medical School, Jerusalem, Israel), and *L. major* (LTM p-2, obtained from Dr. David Moser, Temple Univ. Phila, Pa.), but not *L. guyanesis* (MHOM/BR/75/M4147) (FIG. 3B, lanes 3-9). Given the intensity of the hybridization signals, the K39 repeat sequence appeared to be most closely related between *L. chagasi* and *L. donovani* (FIG. 3B, lanes 3 and 7). No hybridization with either probe was observed with *T. cruzi* DNA (FIG. 3, lane 10).

Using *L. chagasi* digested DNA, two Pst I fragments were detected with probe B, indicating the presence of a second copy of the LcKin gene or polymorphism in restriction sites present in the 3' repetitive sequences (FIG. 3B, lane 3). Probe A hybridized to three fragments in each of the Bam HI, Hind III, and Pst I digests of *L. chagasi* DNA (FIG. 3A, lanes 1-3). Taken together, the Southern blot data show that the LcKin gene is present in a minimum of 2-3 copies in the *L. chagasi* genome, and that related sequences are present in the seven species of Leishmania examined.

EXAMPLE 2

This example illustrates the identification of native LcKin antigen. Rabbit anti-rK39 serum was used to probe SDS-PAGE blots of *L. chagasi* promastigote and tissue amastigote lysates to partially characterize native LcKin protein. Promastigotes were cultured in axenic media. Tissue amastigotes were obtained from spleens of Syrian hamsters or footpads of Balb/c ByJ mice and purified as described in Burns et al. (*J. Immunol.* 146:742, 1991). Rabbit anti-rK39 serum was obtained by subcutaneous immunization of an adult New Zealand white rabbit (R & R Rabbitry, Stanwood, Wash.) with 200 µg of purified rK39 administered in Freund's incomplete adjuvant (IFA; Gibco, Grand Island, N.Y.) together with 100 mg of N-acetylmuramyl-L-alanyl-D-isoglutamine (muramyl dipeptide, Calbiochem, San Diego, Calif.). Five weeks later, the rabbit was boosted with 200 µg rK39 in IFA alone. Four weeks later, the rabbit was boosted intravenously with 25 µg of purified rK39. The rabbit serum was collected 6 days later.

Figure 4A:
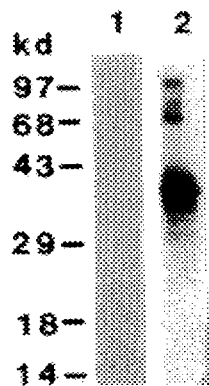
Figure 4B:
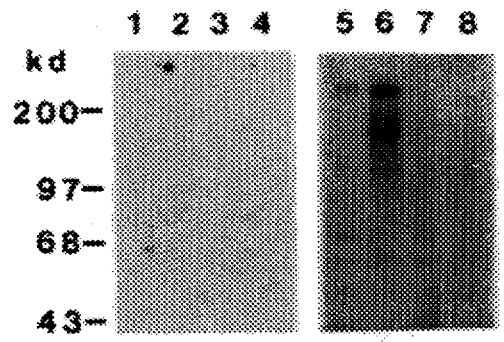
Figure 4C:

The antiserum bound specifically to purified rK39 (FIG. 4A, lane 2) and to an approximately 230 kDa antigen present in amastigotes (FIG. 4B, lane 6) and to a lesser degree in promastigotes (FIG. 4B, lane 5). No reactivity with this serum was detected in promastigote and amastigote lysates of *L. amazonensis* (FIG. 4B, lanes 7-8) indicative of the variability within this repeat. Comparable amounts of lysate were loaded in all lanes as shown by reactivity of a rabbit antiserum raised against a constitutively expressed *L. chagasi* ribosomal phosphoprotein, Lc P0 (Skeiky et al., *J. Exp. Med.* 176:201, 1992) (FIG. 4C, inset). No reactivity was apparent in pre-immune serum (FIG. 4A, lane 1, FIG. 4B lanes 1-4).

EXAMPLE 3

Figure 2:
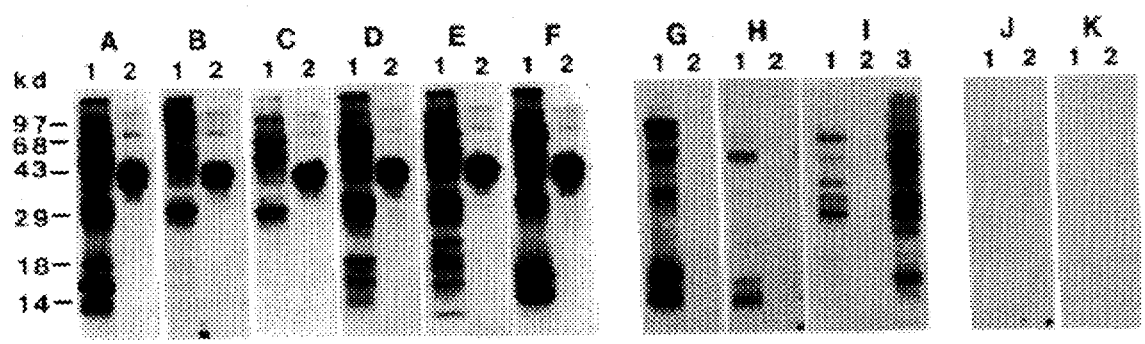

This example illustrates the reactivity of patient sera to recognize the rK39 antigen. Patient sera were obtained from well characterized Brazilian visceral, cutaneous and mucosal patients as well as *T. cruzi* infection sera from a study area in Bahia, Brazil. African visceral and cutaneous leishmaniasis sera were from biopsy-positive patients in the Sudan. Normal sera were from clinically healthy individuals living in endemic areas of the Sudan or from the U.S. The sera were analyzed by an immunoblot assay. Immunoblots of parasite lysates or purified rK39 were prepared as described in Burns et al. (*J. Immunol.* 146:742, 1991). Filters were blocked with TBS containing 5% non-fat dried milk and probed with patient sera (1:250) or rabbit sera (1:400) diluted with TBS with 0.1% Tween-20 and 1% bovine serum albumin. Bound antibody was detected with $^{125}$I-labeled Protein A ($1 \times 10^6$ cpm/blot) followed by autoradiography. Both rK39 and *L. chagasi* promastigote lysates were strongly recognized by *L. chagasi* (FIGS. 2 A-C) and *L. donovani* (FIGS. 2 D-F) infection sera. Reactivity with rK39 was not observed with pools of sera obtained from mucosal (FIG. 2G) or cutaneous (FIG. 2H) leishmaniasis patient sera or with a pool of Chagas' disease (e.g., *T. cruzi*) patient sera (FIG. 2I). The pools of sera obtained from mucosal or cutaneous leishmaniasis Chagas' disease patient sera reacted strongly with promastigote lysates. These data indicate that the K39 antigen is specific to *L. chagasi* and *L. donovani* and/or K39 induces a strong antibody response only in VL patients.

EXAMPLE 4

This example illustrates reactivity of patient sera with rK39 as determined by an ELISA. The patient sera were obtained as described in Example 3. The ELISA was conducted by diluting rK39 or *L. chagasi* promastigote lysate in coating buffer (15 mM $Na_2HCO_3$, 28 mM $NaH_2CO_3$, pH 9.6) to 1 µg/ml or 20 µg/ml, respectively. Microassay plates (Probind, Falcon, Lincoln Park, N.J.) were sensitized with rK39 (50 ng) or promastigote lysate (1 µg/ml) by overnight incubation at 4° C. Plates were blocked with PBS plus 1% Tween-20 for 1 hr at room temperature. After five washes with PBS containing 0.1% Tween-20 (PBS-T), 50 µl per well of sera diluted 1:100 with PBS-T were incubated for 30 min at room temperature. The wells were again washed five times with PBS-T and bound antibody was detected by Protein A-HRP (Zymed, So San Francisco, Calif.) as described in Reed et al. (*Am. J. Trop. Med. Hyg.* 43:632, 1990). Absorbance values are relative to the mean of five control sera assayed on each plate. ELISA values of at least three standard deviations greater than the mean absorbance of the normal control sera were considered positive.

Figure 5A:
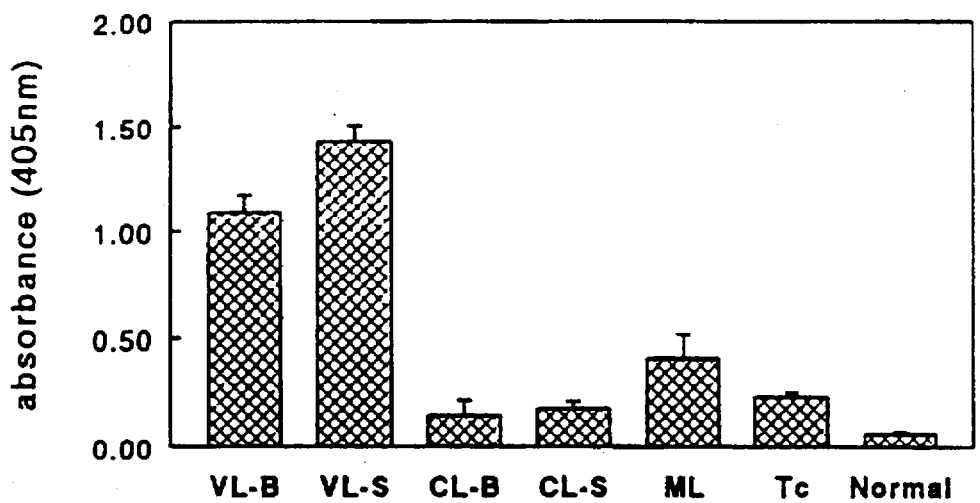
Figure 5B:
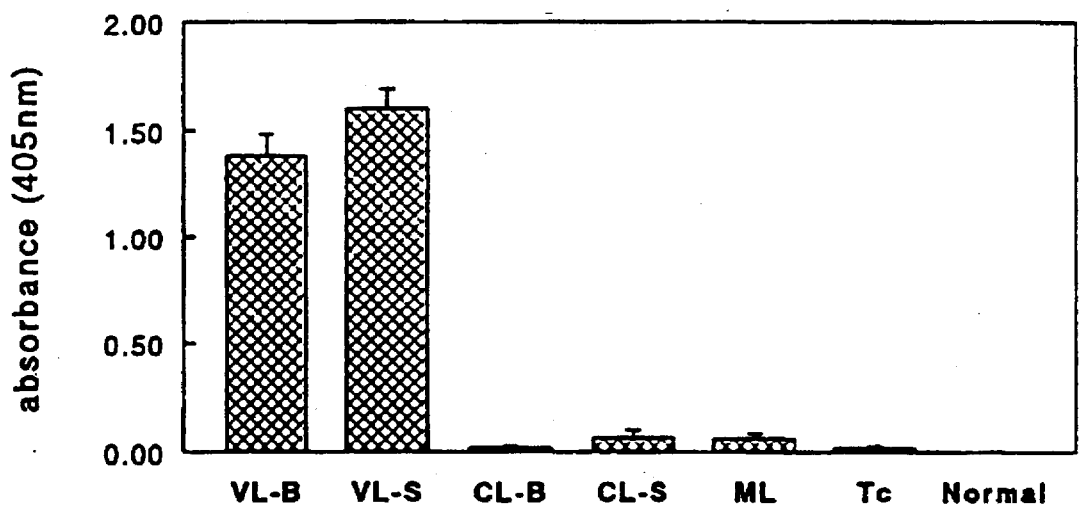

I observed a high level of reactivity among VL patients with 98.2% (56 of 57) of Brazilian VL sera and 100% (52 of 52) of Sudanese VL sera exhibiting positive absorbance values. The positive absorbance values ranged from 0.05 to >2.0 (mean=1.38) among Brazilian VL sera (FIG. 5A) and from 0.094 to >2.0 (mean=1.60) among Sudanese sera (FIG. 5B). Detectable antibody to rK39 was restricted to VL patients, as little or no anti-rK39 response was observed in sera from mucosal or cutaneous leishmaniasis patients or *T. cruzi* infection sera, despite some reactivity in these latter samples with crude *L. chagasi* lysate (FIG. 5).

EXAMPLE 5

This example illustrates a method for producing and purifying recombinant gp63 (rgp63). Recombinant gp63 from *L. chagasi* and *L. donovani* was produced in *E. coli* as a non-fusion protein using T7 RNA polymerase expression system and pET plasmid expression vectors as described in Button et al. (*Mol. Biochem. Parasitol.* 44:213, 1991). Induced bacterial pellets were resuspended in lysis buffer (LB, 50 mM Tris HCl, pH 8.0, 100 mM NaCl, 10 mM EDTA) and lysed by treatment with lysozyme and sonication. The inclusion body fraction containing rgp63 was recovered by centrifugation for 5 min at 200×g and washed twice in LB with 4M urea as a chaotropic agent. The final pellet containing rgp63 was solubilized in 100 mM Tris, pH 8.5, containing 8M urea and 100 mM dithiotreitol. Following dialysis, rgp63 was isolated by ammonium sulfate fractionation, followed by preparative isoelectric focusing in the presence of 8M urea with 3/10 ampholytes using a Rotofor IEF cell (Bio-Rad, Richmond, Calif.) as described in Reed et al. (*Am. J. Trop. Med. Hyg.* 44:272, 1991). Protein concentrations of rgp63 were determined using the Pierce BCA protein assay (Pierce, Rockford, Ill.) and purity assessed by silver-staining (Bio-Rad) after SDS-PAGE as described in Laemmli (*Nature* 227:680, 1970).

I claim:

1. An isolated antigen having a molecular weight of approximately 230 kD which is present in *Leishmania chagasi* and *Leishmania donovani*, and which comprises an amino acid sequence as set forth in SEQ ID NO:2.

2. An isolated polypeptide comprising one or a plurality of K39 repeat antigens having an amino acid sequence set forth in SEQ ID NO:3.

* * * * *